United States Patent
Vorderwülbecke

(10) Patent No.: US 12,029,771 B2
(45) Date of Patent: Jul. 9, 2024

(54) NEEM FOR TREATMENT OF RLS

(71) Applicant: Martin Vorderwülbecke, Munich (DE)

(72) Inventor: Martin Vorderwülbecke, Munich (DE)

(*) Notice: Subject to any disclaimer, the term of this patent is extended or adjusted under 35 U.S.C. 154(b) by 0 days.

(21) Appl. No.: 18/384,489

(22) Filed: Oct. 27, 2023

(65) Prior Publication Data

US 2024/0050508 A1    Feb. 15, 2024

Related U.S. Application Data

(63) Continuation of application No. 17/255,307, filed as application No. PCT/EP2019/066240 on Jun. 19, 2019, now abandoned.

(30) Foreign Application Priority Data

Jun. 26, 2018 (EP) .................................. 18179863

(51) Int. Cl.
| | |
|---|---|
| A61K 36/58 | (2006.01) |
| A61K 31/343 | (2006.01) |
| A61K 31/352 | (2006.01) |
| A61K 31/58 | (2006.01) |
| A61K 45/06 | (2006.01) |
| A61P 25/14 | (2006.01) |

(52) U.S. Cl.
CPC ............ *A61K 36/58* (2013.01); *A61K 31/343* (2013.01); *A61K 31/352* (2013.01); *A61K 31/58* (2013.01); *A61K 45/06* (2013.01); *A61P 25/14* (2018.01); *A61K 2236/15* (2013.01)

(58) Field of Classification Search
None
See application file for complete search history.

(56) References Cited

U.S. PATENT DOCUMENTS

| | | |
|---|---|---|
| 5,370,873 A | 12/1994 | Udeinya |
| 5,900,493 A | 5/1999 | Nagasampagi et al. |
| 2004/0191337 A1 | 9/2004 | Behl et al. |

FOREIGN PATENT DOCUMENTS

| | | |
|---|---|---|
| EP | 3284462 A1 | 2/2018 |
| KR | 20110037462 A | 4/2011 |
| WO | 9417815 A1 | 8/1994 |
| WO | 9725867 A1 | 7/1997 |

OTHER PUBLICATIONS

Balaji, et al.: "Medicinal uses of neem (Azadirachta indica) in human life: a Review", Int. J. of Life Sciences, A10 (2018), pp. 181-184, XP055523471.
Conrick, John: "Neem, the Ultima Herb", 3rd Edition (2009), selected pages.
Gamaldo and Earley: "Restless Legs Syndrome. A Clinical Update", CHEST Postgraduate Education Corner, Contemporary Reviewes in Sleep Medicine, 130(5), (2006), pp. 1596-1604.
NUSnews Press Release: "NUS-led study: Consumption of a bioactive compound from Neem plant could significantly suppress development of prostate cancer", Sep. 28, 2016, NUS115, pp. 1-2.
Pankaj, et al.: "Review on Neem (Azadirachta Indica): Thousand Problems One Solution", International Research Journal of Pharmacy ISSN 2230-8407, 2(12), (2011). pp. 97-102, XP055523468.
Ramar and Olson: "Management of Common Sleep Disorders", American Family Physician, 88(4), (2013), pp. 231-238.
Tomar, et al.: "Neem in Health and Cosmetics" in "Neem. A Treatise", K.K.Singh, et al. (ed.). I.K. Int'l Publ. House, (2009), pp. 461-485.
Blood Purifier Herbal Supplement by Isha Agro Develpers, India, publ. by MINTEL, product description, (2023), pp. 1-3, www.gnpd.com.
Neem Leaf Powder by KOFPU, India, publ. by MINTEL, product description, (2023), pp. 1-3, www.gnpd.com.

*Primary Examiner* — Bong-Sook Baek

(74) *Attorney, Agent, or Firm* — Norton Rose Fulbright US LLP; James R. Crawford

(57) ABSTRACT

A pharmaceutical product of the present invention contains plant parts obtained from the neem tree *Azadirachta indica* or active ingredients derived from such plant parts for use in treating, preventing and/or alleviating symptoms of restless legs syndrome.

14 Claims, No Drawings

NEEM FOR TREATMENT OF RLS

CROSS-REFERENCE TO RELATED APPLICATIONS

This application is a continuation of U.S. patent application Ser. No. 17/255,307 filed Dec. 22, 2020, pending, which is a national phase application under 35 U.S.C. § 371 of International Application No. Application PCT/EP2019/066240 filed Jun. 19, 2019, which claims the benefit of priority from European Patent Application No. 18179863.8 filed Jun. 26, 2018, the entire contents of each of which is incorporated herein by reference in its entirety.

DESCRIPTION

The present invention relates to a pharmaceutical product containing plant parts of the neem tree or active ingredients derived therefrom for use in treating, preventing and/or alleviating symptoms of restless legs syndrome (RLS).

BACKGROUND OF THE INVENTION

The neem tree, *Azadirachta indica*, originates from the Indian subcontinent but also grows well in other, preferably dry regions around the world. It is considered one of the most important medicinal plants and has been used for thousands of years for treating diseases or other adverse conditions in humans and animals, but also as a plant protectant. Plant parts of the neem tree or products obtained therefrom have been found to exhibit antibacterial, antiviral, antifungal, anti-inflammatory, antipyretic, antihistamine and antiseptic properties as well as further desirable characteristics for treating or alleviating diseases, disease symptoms or for other uses to promote health and well-being.

To name merely a few examples of the known applications, in traditional medicine and foremost the Indian Ayurveda, but also in modern medicine various plant parts of the neem tree have been used for treating skin diseases, combatting lice, to promote dental and oral hygiene, for treating psychotic diseases, anemia, high blood pressure, hepatitis, ulcers, thyroid disorders, indigestion, high cholesterol levels, diabetes, inflammation and cancer, and further, neem was also used as a contraceptive agent.

Neem has also been proposed for the treatment of AIDS, arthritis, heart diseases, and malaria and it could be shown that neem extracts are toxic to viruses like herpes virus and can easily heal cold sores. The more recent research relating to the neem tree and its plant parts aimed at extracting and characterizing constituents from plant parts and to attribute certain effects of the neem tree to such individual compounds or compositions containing such compounds. E.g., WO 2015/035199 A1 discloses neem compositions containing certain neem ingredients and their use for alleviating symptoms of cancer. Recently, the University of Singapore published results of a study program according to which a prostate tumor could be reduced by 50% due to treatment with neem (https://news.nus.edu.sg/press-releases/nus-led-study-consumption-bioactive-compound-neem-plant-could-significantly-suppress). The effect was attributed to the active ingredient nimbolide of the neem plant which was found to target glutathione reductase in prostate cancer, an enzyme which is responsible for maintaining the antioxidant system that regulates the STAT3 gene in the body. The activation of the STAT3 gene had been reported to contribute to prostate tumour growth and metastatis, and the scientists at the university observed that nimbolide can substantially inhibit STAT3 activation and thus prevent disease progression.

For a more detailed summary of potential uses, the book "*Neem. A Treatise*", K. K. Singh, Suman Phogat, Alka Tomar, R. S. Ehillon, I. K. International Publishing House, New Delhi, Bangalore, comprehensively lists diseases which have been treated by neem. Further information and an abundance of references to relevant literature and patent documents relating to neem can be found in "*Neem, the Ultima Herb*" by John Conrick, $3^{rd}$ edition, 2009, and also the internet provides a wealth of information regarding the neem tree and its various traditional or more modern uses.

Within the last years, the disease "restless legs syndrome" (RLS) has been recognized as an independent illness or syndrome. Persons affected by this syndrome suffer from a strong urge to move their legs due to an unpleasant feeling in the legs that improves somewhat with moving them. While mostly the legs of patients are affected, sometimes the disease manifests itself also in the arms.

The disease occurs in varying severity and characteristic sensations range from a pain to an aching in the muscles, itching sensations or a buzzing, tickling, crawling feeling or even an involuntary jerking of the legs. While some affected persons experience only minor symptoms and impairments, others suffer severely and their quality of life can be significantly impaired. For example, patients tend to avoid longer-term motionless phases, and the syndrome causes business meetings and conferences, air travel and also cultural activities like visits to the theater to be at least unpleasant, sometimes even unbearable. Disease sequels like sleep deprivation can occur since the unpleasant sensations make it difficult to sleep or cause sleep disturbance which in turn leads to daytime sleepiness, low energy, irritability and depressed mood. As impending further consequence, patients are at risk to even lose their employment due to the complications caused by the syndrome.

According to information provided by the German Society for Neurology (Deutsche Gesellschaft für Neurologie (DGN), Leitlinie 2012), in Germany 3 to 10% of the population is affected by restless legs syndrome. Further, according to Ramar, K.; Olson, E. J., "*Management of Common Sleep Disorders*", American Family Physician, 88(4): 231-8, 2013 and Gamaldo, C. E., Earley, C. J. "*Restless Legs Syndrome: A Clinical Update*", Chest. 130 (5): 1596-604, 2006, 2.5 to 15% of the American population is affected by RLS. A minority of these affected persons is reported to experience severe symptoms daily, and further the syndrome was found to be twice as common in women as in men.

Taking into account these data, the RLS syndrome is one of the most prevalent neurological disorders. While some affected persons only experience weak symptoms which do not necessarily have to be treated, the percentage of persons that require treatment was considered for the USA to be about 2.7% of the population. Accordingly, RLS has to be considered a mass phenomenon for which, unfortunately, no causal treatment is available, yet. While quite a number of causes of illness have been considered, for the time being only a suppression of symptoms is possible. To this purpose, mainly two types of medicaments containing single substances or substance compositions are available:

a) L-Dopa, trade name Restex®, active ingredient Levodopa/Benserazid, presently being considered the means of choice; and
b) Dopamine agonists, like Adartrel® (Ropirinol), Sifrol® (Pramipexol) and Neupro® (Rotingotin).

In the United States, also gabapentin enacarbil is admitted, however only for treating severe cases of RLS.

Unfortunately, upon treatment with such approved medicaments, severe side effects can occur, e.g. augmentation. Augmentation causes symptoms to expand, reoccur earlier or more intensely. Also, when the treatment with L-Dopa is discontinued, symptoms will recur since no causal therapy is achieved.

Considering the current lack of treatment options pertaining to the actual causes of restless legs syndrome and in view of the side effects which have to be accepted when using the currently available medicaments, there is a need for alternative methods and drugs to control the disease or to at least alleviate the symptoms of RLS without involving severe side effects. Accordingly, it was an object of the present invention to provide such alternative methods and drugs.

SUMMARY OF THE INVENTION

Within the context of the present invention, it was discovered that plant parts obtained from the neem tree or active ingredients derived from such plant parts can be a successfully used to combat the symptoms of restless legs disease. The subject matter of the present invention, accordingly, is a pharmaceutical product containing plant parts obtained from the neem tree *Azadirachta indica* or active ingredients derived from such plant parts for use in treating, preventing and/or alleviating symptoms of restless legs syndrome (RLS).

While the neem tree and products obtained from neem tree have been applied and described for the treatment of numerous diseases and ailments, this plant has never been considered in the context of RLS. Surprisingly it has now been found that the symptoms experienced by patients affected by the disease can very effectively be reduced or even completely obviated when such patients are treated with neem products. Especially when compared with the currently applied treatment, use of neem products to treat the disease provides advantages without serious side effects. Quite to the contrary, for hundreds of years neem products have proven to be well tolerated medicaments if applied in a responsible manner.

Further subjects and preferred embodiments of the invention will be described in the following.

DETAILED DESCRIPTION OF THE INVENTION

The pharmaceutical product which, according to the present invention, is intended for use in treating, preventing and/or alleviating symptoms of RLS can be derived from any part of the neem tree plant. Neem plant parts which can be considered as pharmaceutically applicable substances are especially leaves, flowers, seed, fruit, gum or bark of the neem tree.

The plant parts can be obtained, processed and/or purified as best adapted to the respective plant part and to the intended manner of application for medical treatment. Processes and conditions to obtain plant parts and to manufacture drugs of such plant parts are well known to the skilled person as is apparent from the many publications that are available concerning the application of neem in the traditional and also the modern medicine. While the present invention is directed to a novel and highly valuable new medical use of neem, all so far applied or considered forms and manners of application of neem are also applicable within the context of the present invention.

In a preferred embodiment of the present invention, neem tree leaves are used to prepare the pharmaceutical product of the present invention. To this purpose, neem leaves preferably are dried and then further processed to be crushed to a powder, shredded or reduced to small ingestible pieces of the leaves. Neem leaves processed in such manner can very well be administered orally without any adverse side effects. Even a product containing whole or only slightly crushed leaves to be chewed on is a useful application form in order to profit from the effects of the neem leaves. Alternatively, fresh neem leaves can be pressed and the resulting juice be used for application.

While the leaves can be ingested completely or in a shredded or crushed form, preparing at tea is a further option to arrive at a pharmaceutical product according to the present invention. Such tea can be either prepared from whole leaves, fresh or dried, or from shredded or ground leaves by adding hot water and letting it brew for an appropriate span of time.

According in a further preferred embodiment of the invention, active ingredients are obtained by extraction to provide the pharmaceutical product. The extraction process can be adapted to obtain a crude extract, containing a complex mixture of substances. Furthermore, the extraction process can be adapted to partly or completely isolate substances which are active ingredients of the neem tree. For example, if substances are only partly isolated, the process can be adapted to extract and isolate a certain group of (e.g. chemically similar) substances whereas a complete isolation means that only one active substance is ultimately obtained. Methods for extracting active ingredients from plant parts of neem have been described in various publications. In principle, all methods for providing extracts from plants are applicable within the context of the present invention. As examples, it is referred to WO 94/17815, WO 97/25867, U.S. Pat. No. 5,900,493 and as a more recent document to WO 2015/035199 A1.

Ingredients of neem which are considered as pharmaceutically active and which can be isolated either singly or in a mixture of two or more of such substances are nimibin, nimbinin, nimbidin, salannin, melilantriol and azadirachtin. Accordingly, a pharmaceutical composition containing at least one of such active ingredients is a further preferred embodiment of the present invention.

In general, internal use as well as external use of neem is applicable within the context of the present invention in order to treat RLS. While oral administration is preferred, for application of active ingredients derived from neem plant parts also other administration routes are in principle useful, e.g. parenteral or rectal application. The pharmaceutical products of the invention are formulated in dosage forms which are appropriate for each such route of administration.

In a further preferred embodiment of the invention, the pharmaceutical product contains additional pharmaceutically active substances or drugs. On the one hand, commonly used analgesic or antiphlogistic/anti-inflammatory substances can be included, however, it is also possible to include any other substance that can provide further advantageous pharmaceutical effects or relief to the patient.

A pharmaceutical product of the invention which is intended for internal use is preferably provided in the form of capsules, tablets, lozenges, pills or granules containing plant parts, most preferably crushed or shredded neem leaves, or active ingredients derived from such plant parts. Apart from such solid form preparations, also liquid preparations in the form of e.g. teas, emulsions, suspensions obtained from plant parts or containing one or more active ingredients are applicable. Suspensions and emulsions can be prepared using aqueous, non-aqueous or mixed media or diluents, and can further include substances to increase the viscosity of such suspensions or emulsions, e.g. sorbitol, dextran or sodium carboxymethylcellulose, as well as stabilizers, wetting agents or other appropriate substances. Also neem extracts or neem oil which is obtained from neem seed can be contained in the pharmaceutical products of the present invention.

Depending on the application form, it can be necessary or useful to include further substances in the pharmaceutical product. On the one hand, such substances can be pharmaceutically acceptable adjuvants and excipients, especially carriers, coatings, fillers, lubricants, glidants, varnish or wax, binders, buffers, but also compounds which ensure easy disintegration, disaggregation and dissolution of tablets in the stomach or the intestine, or substances which provide for a sustained release effect. Considering the bitter taste of neem products, substances selected from one or more of sweeteners, sugars, flavor or perfuming agents are also preferably included in the pharmaceutical products of the invention as well as coloring agents or preservatives.

A further embodiment of the invention concerns the external application of the pharmaceutical product of the invention. For this purpose, the neem plant parts or active ingredients derived from neem plant parts is formulated in an appropriate form, preferably as a paste, cream, balm, ointment, emulsion, suspension, oil, gel, spray or foam. In this context, also the neem oil obtained from neem seed is directly applicable, however, usually needs to be diluted with another suitable oil, preferably a natural oil like olive oil or almond oil.

On the one hand, such product for external use can be applied to especially the legs of the patients or to any other extremities in which the patient experiences discomfort or pain associated with RLS. To obtain best results in alleviating RLS symptoms in patients, the pharmaceutical product for external application is preferably formulated to be capable of penetrating the skin and, more preferably, being absorbed into the blood circulation or the lymphatic system. Suitable formulations are known to the skilled person and provide for a local as well as an overall systemic effect.

Also the pharmaceutical products of the invention which are intended for external use can contain further pharmaceutically active substances or drugs, which have further advantageous pharmaceutical effects, preferably analgesic and/or antiphlogistic/anti-inflammatory substances. Adjuvants, excipients and preservatives as described above, but also other substances like scents to provide for a pleasant smell of such products and coloring agents as well as preservatives can beneficially be included in the products of the invention.

For neem containing cream-like pharmaceutical products, it is preferred to include neem oil as the active ingredient obtained from neem plant parts. The content of neem oil in such creams generally is 1 to 10%, more preferably 2.5 to 7.5%. The pharmaceutical products can be applied several times per day, usually 2 to 5 times, covering the area of discomfort and optionally applying the product over the whole leg.

As with every pharmaceutically active substance, responsible treatment is required also within the context of the present invention in order not to cause unwanted effects. As neem has been used in different forms for medical treatment for a very long time, dosages for use within the context of the present invention can be adapted to ensure that no negative side effects occur. On the other hand, it is well known to the skilled person which dosages are required to allow for a medicinal effect to be observed. While many persons easily tolerate application of neem in usually recommended amounts, for other persons it will be advantageous to start out with lower dosages and to increase the application dosage of the pharmaceutical product over a few days or weeks to arrive at the intended medicine intake or uptake.

In a very preferred embodiment of the invention, the pharmaceutical product is in the form of a capsule containing crushed or powdered neem leaves for oral application. Any pharmaceutically useful form of such capsules can be chosen and a content of cleaned neem leaves in such capsules is preferably from 100 to 1000 mg, more preferably from 300 to 600 mg.

A recommended application dosage of such crushed or powdered neem leaves is from 500 to 5000 mg per day, although the dosage can be increased or decreased depending on the effect observed in the patient.

It has been observed by the inventor that the neem plant and products obtained therefrom can be advantageously applied for treatment of RLS. Patients suffering from RLS and treated with the pharmaceutical products of the invention experienced strong relief of RLS symptoms soon after treatment initiation and without any side effects. Consequently, these treated patients were able to sleep better, but also to generally stay still for much longer periods of time without experiencing the urge to move especially their legs or severe discomfort. The treated patient experienced improved life quality compared to the time before the treatment was started.

The following Examples further illustrate the present invention:

Example 1

Treatment of Patient: Case No. 1, Male, 58 Years Old (German)

The patient was diagnosed when 52 years old as having a "very lively" form of RLS. The diagnosis was made by a German neurologist. The diagnosis was further confirmed by treating the patient with L-Dopa, which is considered as best practice in treating RLS. If the symptoms decrease or cease under exposure to L-Dopa, the diagnosis is considered confirmed which was the case for this patient. Unfortunately, however, the symptoms did not completely cease and the continued treatment with L-Dopa was also considered undesirable.

The patient then started to take neem capsules contained dried neem leaves which are available on the market in different forms and brands. Each capsule contained 500 mg of dried neem leaves. For over 18 months, the patient took two capsules of dried neem leaves two times daily which amounts to 2 g of dried neem leaves per day.

Under this treatment, the symptoms of RLS disappeared completely. If the treatment was stopped, the symptoms started to reappear after a few days. When reinitiating the treatment, the symptoms disappeared again. This effect of the treatment and discontinuing of the treatment was confirmed several times and proved that the treatment is responsible for the disappearance of the symptoms of RLS.

Example 2

Treatment of Patient: Case No. 2, Female, 74 Years Old (Turkish)

The second patient suffered from RLS for many years. The patient is treated by neem leaves, a tea spoon each night. Since the patient has started this treatment, she considers herself free of symptoms of RLS during the night.

Also this patient observed reappearance of symptoms if the treatment was discontinued which again proves the effect of the neem leaves on the encumbering RLS symptoms.

What is claimed is:

1. A method of treating or alleviating symptoms of restless legs syndrome (RLS) comprising administering to a subject in need thereof a therapeutically effective amount of a pharmaceutical product containing plant parts obtained from neem tree (*Azadirachta indica*) leaves.

2. The method according to claim 1, wherein the pharmaceutical product comprises crushed or shredded neem tree leaves.

3. The method according to claim 1, wherein the pharmaceutical product is provided in a dosage form suitable for internal use.

4. The method according to claim 3, wherein the pharmaceutical product is in dry or liquid form.

5. The method according to claim 1, wherein the pharmaceutical product further comprises additional pharmaceutically active substances or drugs.

6. The method according to claim 1, wherein the pharmaceutical product further comprises pharmaceutically acceptable adjuvants and excipients.

7. The method according to claim 1, wherein the pharmaceutical product is provided in a form suitable for external use.

8. The method according to claim 7, wherein the pharmaceutical product is in the form of a paste, cream, balm, ointment, emulsion, suspension, gel, spray or foam.

9. The method according to claim 7, wherein the pharmaceutical product penetrates the skin and/or is absorbed into the blood circulation.

10. The method according to claim 7, wherein the pharmaceutical product further comprises additional pharmaceutically active substances or drugs.

11. The method according to claim 7, wherein the pharmaceutical product further comprises substances selected from the group consisting of pharmaceutically acceptable adjuvants, excipients and preservatives.

12. The method according to claim 1, wherein the pharmaceutical product further comprises at least one member selected from the group consisting of a filler, a lubricant, a glidant, a binder, a compound which ensures disintegration of the pharmaceutical product, a compound providing for sustained release of the pharmaceutical product, a sweetener, a sugar, a varnish, a wax, a flavor, a coloring agent and a preservative.

13. The method according to claim 1, wherein the pharmaceutical product is a tablet, and wherein the pharmaceutical product further comprises a compound which ensures disaggregation and dissolution of the tablet in the stomach or the intestine.

14. The method according to claim 1, wherein the pharmaceutical product is a powder, a granule, a pill, a tablet, a lozenge, a capsule, an emulsion, a suspension, an extract, an oil, a tea and tea preparation.

* * * * *